Figure 1:
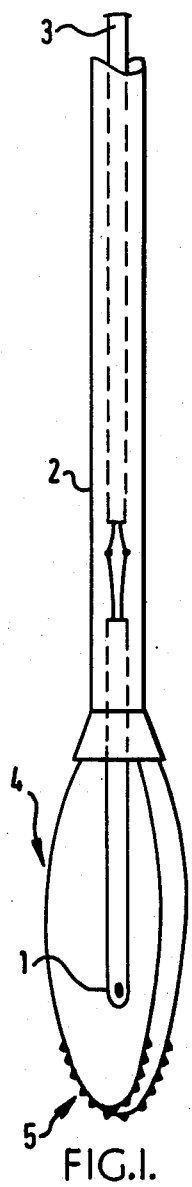

United States Patent [19]

Molloy

[11] 4,400,096

[45] Aug. 23, 1983

[54] OSMOMETERS

[76] Inventor: Robert E. Molloy, 52 Cholmeley Crescent, London N6, England

[21] Appl. No.: 269,263

[22] Filed: Jun. 1, 1981

[30] Foreign Application Priority Data

Jul. 16, 1980 [GB] United Kingdom ............... 8023166

[51] Int. Cl.³ ..................... G01N 25/14; G01N 15/06
[52] U.S. Cl. ...................................... 374/25; 73/64.3
[58] Field of Search .................... 73/64.3; 374/25, 16; 23/301; 422/254; 210/927, DIG. 24; 15/236 R

[56] References Cited

U.S. PATENT DOCUMENTS 3,203,226  8/1965  Fiske, Jr. ..................... 73/64.3 X
3,205,699  9/1965  Van Assendelft ................ 374/16
3,667,280  6/1972  Simpson ............................. 374/25
4,304,119  12/1981  Uchigaki ........................... 374/25

FOREIGN PATENT DOCUMENTS 2951709  7/1981  Fed. Rep. of Germany ....... 73/64.3

Primary Examiner—E. R. Kazenske
Assistant Examiner—Joseph W. Roskos
Attorney, Agent, or Firm—Hayes, Davis & Soloway

[57] ABSTRACT

An osmometer probe comprises a cage which carries abrasive material and encloses a temperature sensor. In use, the probe is placed in a super-cooled solution and the abrasive material detaches particles of the container which initiate crystallization of the solution, the temperature on crystallization being measured by means of the temperature sensor.

6 Claims, 2 Drawing Figures

U.S. Patent    Aug. 23, 1983    4,400,096

OSMOMETERS

This invention relates to devices for determining the concentration of particles of a solute in a solvent, commonly known as osmometers.

"Particle" here refers not only to molecules of the solvent but to molecular fractions, atoms or ions in the case of a solute which dissociates.

The number of particles per kilogram of solution is called "osmolality" and is a quantative measure of the number of dissolved particles, without regard to their identities. This measure is widely used in intensive care medicine, in the management of seriously ill patients. Comparison of the osmolality of the blood plasma with that of the urine gives accurate information about kidney function and aspects of pituitary hormone activity. These measurements may be required several times a day, for a seriously ill patient. Such measurements are also applicable to non-medical fields where accurate measurements of low concentrations of solutes are needed, for example in monitoring water polution.

The presence of a solute in a solvent causes several properties of the solution to change by amounts dependent on the concentration of solute particles. The property most commonly used to determine osmolality is the freezing point of the solution, which is lowered by the presence of a solute. In this method, a small sample of the solution is cooled at a standard rate to below its estimated freezing point. When this super-cooled state is reached the solution is agitated or disturbed in such a way that the process of crystallisation is initiated. The temperature of the crystallising mass then rises to a freezing 'plateau' which remains constant while latent heat of crystallisation is exchanged. A precise measurement of the temperature during this plateau period gives an excellent and reproducible measure of osmolality when comparisons are made with standard solutions.

According to the present invention, the temperature of the solution is sensed by a probe provided with abrasive or cutting means, by which in use particles are detached from the interior of the container in which the solution is placed, to act as nuclii for initiating crystallisation of the super cooled solution.

According to another aspect of the invention, the temperature of the solution is monitored and a signal is provided when the temperature reaches a predetermined value, whereupon crystallisation of the super cooled solution is initiated. Initiation can be effected by means of a temperature-sensing probe, manually by an operator or automatically.

Figure 2:
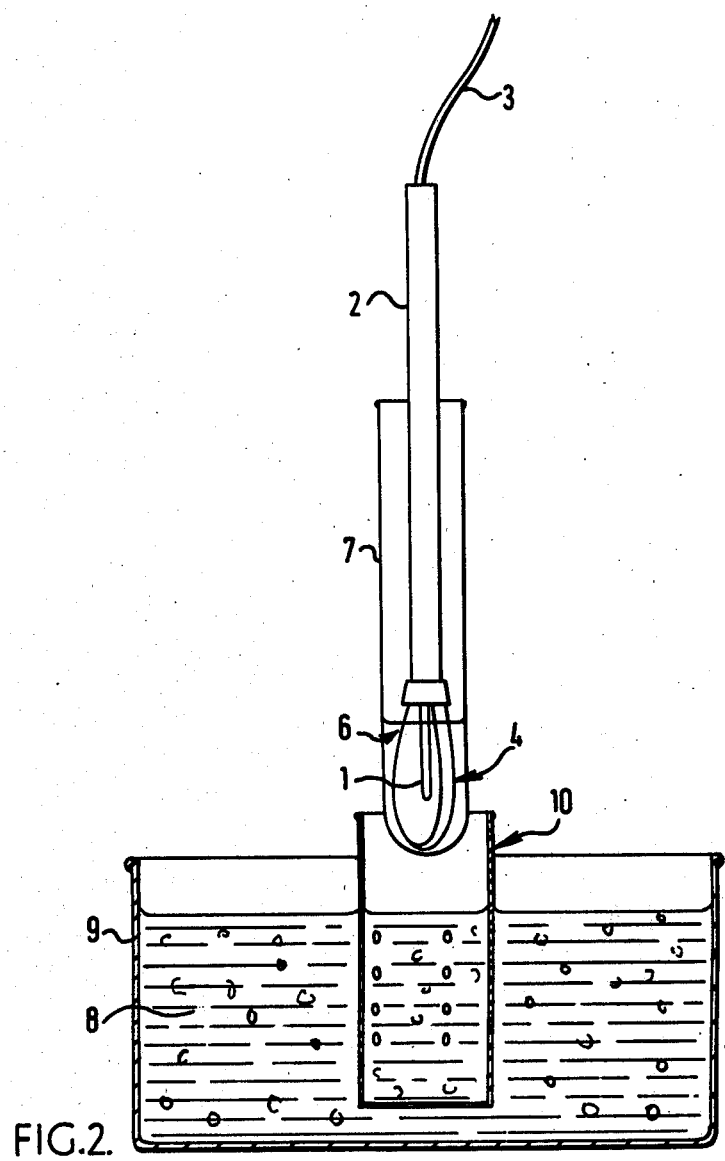

An osmometer embodying the invention is illustrated by the accompanying drawing, in which FIG. 1 shows a probe and FIG. 2 shows, on a smaller scale, the probe with a sample tube and cooling means.

FIG. 1 shows a temperature-sensing probe comprising a glass bead thermistor 1 mounted on and projecting from the end of a tubular mount or handle 2. Electrical leads 3 connected to the thermistor extend through the tubular mount for connection to electronic measuring circuitry.

Thermistor is enclosed by a cage 4 consisting for example of three or more bars made of wire, metal strip, or other material inert to the solutions to be tested. Preferably the cage is slightly flexible.

On the outside of the cage there is an abrasive material 5.

In use, a small sample 6 of the solution of which the osmolality is to be measured is put in a container or sample tube 7 (FIG. 2) and the thermistor probe is inserted into the tube. The cage 4 protects the thermistor and holds it in the centre of the sample.

The tube is then immersed in a cooling medium 8 in a container 9 provided with a perforated central tube 10 which receives the container.

The cooling medium is preferably a slush, prepared by refrigeration of a solution of sodium chloride or other substance. The slush has a constant melting temperature depending on the concentration of salt used, and provides standardised cooling conditions.

The thermistor is connected by the lead 3 to an electronic monitoring instrument which provides a signal when the temperature of the sample has fallen to a predetermined level, below the estimated freezing point of the sample. When this signal is given, the temperature probe is rotated or otherwise moved in the sample tube and the abrasive material 5 scratches the inside of the container, detaching spicules of the container which form microscopic nuclii or seeds, whereby crystallisation of the super cooled sample is reliably and rapidly initiated, spreading throughout the sample.

In consequence of the crystallisation of the sample, its temperature rises promptly to the freezing "plateau" described above. This temperature rise indicates that crystallisation has occurred and the previously mentioned signal is thereby cancelled. The electronic instrument then measures the sample temperature sensed by the thermistor probe and provides an output, preferably in terms of milliosmols per kilogram.

The rotation of the probe can be done manually by an operator, in which case the signal from the electronic instrument will be a visible or audible signal to the operator. Alternatively, the signal from the monitoring circuitry may automatically initiate rotation of the probe for example by a small electric motor.

The monitoring instrument may provide its output in the form of a visual display and/or print.

The freezing of the cooling medium can be carried out independently, or refrigerating means may be incorporated in the osmometric instrument.

A fully automatic osmometer may be provided incorporating refrigerating means as just mentioned, a drive for automatic movement of the probe when the sample temperature has fallen to a suitable value, and automatic conversion of the sensed temperature into a measure of osmolality.

It will be understood that the materials used for the probe, including the abrasive material, must be inert to the solutions to be tested.

The abrasive material, or equivalent cutting means for detaching particles from the sample container, should be placed at whatever position on the probe will most reliably and conveniently ensure the separation of seeding particles from the sample container. An example of a suitable abrasive material is diamond grit. The sample container may for example be a glass tube.

I claim:

1. A device for determining the concentration of particles of a solute in a solvent, comprising a temperature-sensitive probe provided with abrasive or cutting means for detaching particles from the interior of a container for the solution.

2. A device as claimed in claim 1 in which the probe comprises a cage on which the abrasive or cutting means are provided, and a temperature-sensitive element within the cage.

3. A device as claimed in claim 1 or 2 in which the probe is provided with diamond grit as the abrasive means.

4. A device as claimed in claim 1 or 2 in combination with means for monitoring the temperature of the solution, adapted to provide a signal when the temperature reaches a predetermined value.

5. A method of determining the concentration of particles of a solute in a solvent, comprising the steps of super-cooling the solution formed by the solute and solvent and containing the super-cooled solution in a container, inserting into the solution in the container a temperature-sensitive probe provided with abrasive or cutting means, detaching particles from the interior of the container by operation of the abrasive or cutting means thereby initiating crystallisation of the super-cooled solution about the said particles acting as nuclei, and measuring the temperature of the crystallising solution, the said temperature being a measure of the said concentration of particles.

6. The method of claim 5 further comprising monitoring the temperature of the solution by the said probe during the said super cooling of the solution, and initiating the crystallisation of the super cooled solution by the said detaching of particles from the interior of the container, when the sensed temperature of the solution has reached a predetermined super cooled value.

* * * * *